United States Patent [19]
Snader et al.

[11] 3,975,380
[45] Aug. 17, 1976

[54] SUBSTITUTED AURONES
[75] Inventors: Kenneth M. Snader, Hatboro, Pa.;
Chester R. Willis, Blackwood, N.J.
[73] Assignee: SmithKline Corporation,
Philadelphia, Pa.
[22] Filed: June 3, 1974
[21] Appl. No.: 475,726

[52] U.S. Cl. ............................ 260/240 R; 424/285;
260/240 F
[51] Int. Cl.$^2$........................................ C07D 307/83
[58] Field of Search..................... 260/240 F, 240 R

[56] References Cited
FOREIGN PATENTS OR APPLICATIONS
42-24588  12/1964  Japan .............................. 260/240 F OTHER PUBLICATIONS
Saleh et al., J. Chromatography vol. 57, pp. 166–168 (1971).

Khaikin et al., Chemical Abstracts vol. 73, abst. 135912b (1970).

*Primary Examiner*—John D. Randolph
*Attorney, Agent, or Firm*—Richard D. Foggio; William H. Edgerton

[57] ABSTRACT

Substituted aurones useful as inhibitors of certain antigen-antibody reactions, particularly in alleviating allergic manifestations such as asthma, are prepared by reaction of a 3-coumaranone with an appropriately substituted benzaldehyde followed by treatment with aqueous mineral acid and an alkanol.

3 Claims, No Drawings

SUBSTITUTED AURONES

This invention relates to novel substituted aurones which are useful as inhibitors of certain antigen-antibody reactions and particularly in alleviating allergic manifestations such as allergic asthma, allergic rhinitis and atopic dermatitis. The compounds of this invention inhibit the release and/or formation of pharmacologically active mediators from effector cells triggered by the interaction of antigen and a specific antibody fixed to the cell surface. Thus the compounds are valuable in the treatment of allergic diseases such as asthma, rhinitis and urticaria.

The compounds of this invention are represented by the following general structural formula:

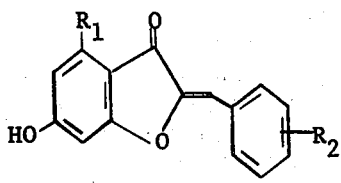

FORMULA I in which:
$R_1$ represents hydrogen or hydroxy; and
$R_2$ represents halogen, such as chlorine, bromine or fluorine, and, when $R_1$ is hydrogen, additionally hydroxy, methoxy or dimethoxy.

Preferred compounds of this invention are represented by formula I above when $R_1$ is hydroxy and $R_2$ is halogen, particularly fluorine.

The compounds of this invention are prepared as shown in the following reaction scheme:

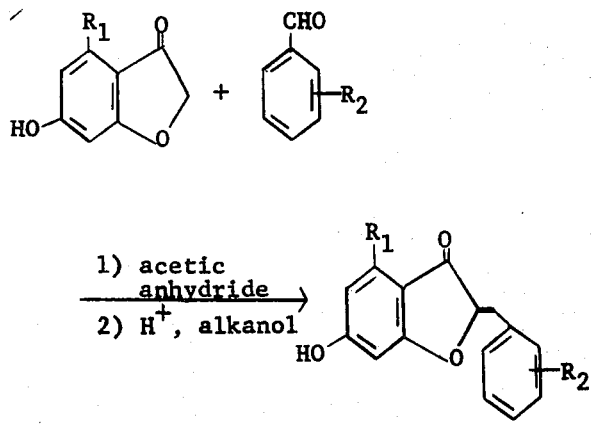

in which $R_1$ and $R_2$ are as defined in formula I. Thus, as shown above, a 3-coumaranone is reacted with an appropriately substituted benzaldehyde and acetic anhydride by heating at a temperature up to about 100°C. for from 1 to 3 hours. The reaction mixture is treated with ice, extracted with a nonreactive organic solvent such as ether and the product from the extract is heated at reflux for about one hour with a mineral acid, such as hydrochloric acid, an alkanol such as methanol or ethanol, and water. Cooling gives the substituted aurone product.

The 3-coumaranone starting materials used as described above are prepared by known methods, for example from resorcinol or phloroglucinol by reaction with chloroacetonitrile in the presence of zinc chloride.

Under the conditions outlined herein, the substituted aurone products generally assume the transoid configuration as shown in formula I. The cisoid isomers can be obtained by photolysis. Although the structural formulas depict the transoid configuration, it is intended to include all isomers, whether separated or mixtures thereof.

The inhibitory activity of the compounds of this invention on mediator release in sensitized tissues is measured by the ability of the active medicament to inhibit the passive cutaneous anaphylaxis (PCA) reaction in rats. In this test system, titered and appropriately diluted serum (from rats previously immunized by the intraperitoneal injection of ovalbuminaluminum hydroxide or ovalbumin-i.m.-Bordatella pertussis U.S.P. i.p.-and N. Brasiliensis i.p.) containing reaginic antibodies directed against ovalbumin is injected intradermally at four sites on the shaved backs of normal adult male rats. Forty-eight hours later the animals are injected intravenously with 0.5 ml. of isotonic saline solution containing 5 mg. of the ovalbumin antigen and 5 mg. of Evans blue dye. Chemical mediators such as histamine and serotonin which are released at the sensitized sites as a result of a local cellular anaphylaxis, cause an increase in capillary permeability with resultant leakage of plasma and formation of a wheal. The wheal is visualized by the plasma protein-bound Evans blue dye. Under conditions of the test, the average control wheal is approximately 12×12 mm. Thirty minutes following antigen challenge, the animals are killed, the dorsal skin is reflected and the diameter of the wheals recorded. A test compound is administered intravenously, initially at 0.5 minutes prior to antigen challenge (longer pretreatment times and other routes of drug administration, i.e. oral or intraperitoneal may be employed). Percent inhibition is calculated from the difference in mean average wheal diameter between a treated group and saline or appropriate diluent controls.

The compounds of this invention administered intravenously to rats at doses of from 0.5 to 10 mg/kg produce marked inhibition of the PCA reaction. A preferred compound, 4,6-dihydroxy-4'-fluoroaurone, produced 42% inhibition of the rat PCA wheal at 0.5 mg/kg, i.v. In testing for mechanism of action, the compounds of this invention were found not to provide comparable inhibition of wheals of equal severity produced in rats by the intracutaneous administration of histamine and serotonin following i.v. administration of the test compound at the same dose and pretreatment time which exhibited significant inhibition of the rat 48-hour PCA reaction.

Another feature of this invention is a pharmaceutical composition comprising an appropriate amount of a substituted aurone as set forth in formula I in association with a pharmaceutical carrier or diluent. The nature of the composition and the pharmaceutical carrier or diluent will of course depend upon the intended route of administration, i.e. orally, parenterally or by inhalation. Preferably a compound is administered to an animal in a composition comprising an amount sufficient to produce an inhibition of the consequences of the antigen-antibody reaction. When employed in this manner, the dosage of composition is preferably such that from 5 mg. to 500 mg. of active ingredient are administered at each administration. Advantageously equal doses will be administered 1 to 4 times daily with the daily dosage regimen being about 5 mg. to about 2000 mg.

In general, particularly for the prophylactic treatment of asthma, the compositions will be in a form suitable for administration by inhalation. Thus the compositions will comprise a suspension or solution of the active ingredient in water for administration by means of a conventional nebulizer. Alternatively the compositions will comprise a suspension or solution of the active ingredient in a conventional liquified propellant such as dichlorodifluoromethane or chlorotrifluoroethane to be administered from a pressurized container. The compositions may also comprise the solid active ingredient diluted with a solid diluent, e.g. lactose, for administration from a powder inhalation device. In the above compositions, the amount of carrier or diluent will vary but preferably will be the major proportion of a suspension or solution of the active ingredient. When the diluent is a solid, it may be present in less, equal or greater amounts than the solid active ingredient.

As a specific embodiment of a useful composition, the active ingredient, such as 4,6-dihydroxy-4'-fluoroaurone, is dissolved in sterile water at a concentration of 0.5% and aerosolized from a nebulizer operating at an air flow adjusted to deliver the desired aerosolized weight of drug.

The invention also includes a method of inhibiting the effects of the antigen-antibody reaction which comprises the prior application to the area of the antigen-antibody mechanism a therapeutically effective amount of a substituted aurone as defined in formula I. A particular application of the invention is a method of relieving or preventing allergic airway which comprises administering to an animal a therapeutically effective amount at suitable intervals.

Substituted aurones are known to the art, for example *Chem. Abstracts* 44:5352a; *J. Am. Chem. Soc.* 78:832-7 (1956); *Chem. Abstracts* 52:17255e; *Chem. Abstracts* 73:135912b; and Japanese Patent 67,24588 (Derwent No. 29852). However there is no disclosure of the compounds of this invention or their use as inhibitors of antigen-antibody reactions.

The foregoing is a general description of how to prepare the compounds of this invention. The following examples illustrate the preparation of specific compounds having antigen-antibody inhibitory activity. However this should not be construed as a limitation of the invention since appropriate variations in the starting materials will produce other products set forth hereinabove.

EXAMPLE 1

A mixture of 3.3 g. (0.02 m.) of 4,6-dihydroxycoumaran-3-one, 2.5 g. (0.02 m.) of p-fluorobenzaldehyde and 50 ml. of acetic anhydride is heated on a steam bath for 90 minutes. The cooled reaction mixture is poured onto ice, extracted with ether and the ether distilled off. The residual liquid is diluted with 50 ml. of 20% aqueous hydrochloric acid and 50 ml. of methanol and then refluxed on a steam bath for 1 hour. The solid which precipitates upon cooling is recrystallized to give 4,6-dihydroxy-4'-fluoroaurone, m.p. 272°–273°C.

Similarly, by employing 6-hydroxycoumaran-3-one as described above there is obtained 4'-fluoro-6-hydroxyaurone, m.p. 251°–252°C.

EXAMPLE 2

Following the procedure of Example 1, equimolar amounts of 6-hydroxycoumaran-3-one and m-hydroxybenzaldehyde are heated with acetic anhydride on a steam bath. After extraction of the cooled reaction mixture and removal of the solvent, the residue is refluxed with dilute aqueous hydrochloric acid and methanol to give the product, 3',6-dihydroxyaurone, m.p. 270°–272°C.

EXAMPLE 3

As outlined in Example 1, 6-hydroxycoumaran-3-one, 2,3-dimethoxybenzaldehyde and acetic anhydride are heated on a steam bath. Similar workup of the reaction mixture followed by heating with dilute aqueous hydrochloric acid and methanol yields 2',3'-dimethoxy-6-hydroxyaurone, m.p. 231°–232°C.

By employing 4-methoxybenzaldehyde in the above described reaction procedure there is obtained 6-hydroxy-4'-methoxyaurone.

EXAMPLE 4

As described in Example 1,4,6-dihydroxycoumaran-3-one, p-chlorobenzaldehyde and acetic anhydride are heated on a steam bath. By following the similar workup procedure there is obtained, after treatment with dilute aqueous hydrochloric acid and methanol, 4'-chloro-4,6-dihydroxyaurone, m.p. 221°–224°C.

Employing p-bromobenzaldehyde in the above reaction sequence yields the corresponding 4'-bromo-4,6-dihydroxyaurone.

What is claimed is:

1. A chemical compound of the formula:

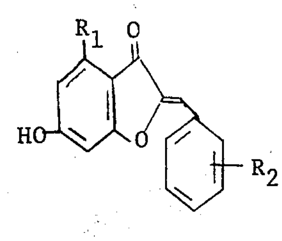

wherein:

$R_1$ is hydrogen or hydroxy; and $R_2$ is fluorine.

2. A chemical compound according to claim 1 in which $R_1$ is hydroxy.

3. A chemical compound according to claim 2 in which $R_2$ is 4'-fluorine, being the compound 4,6-dihydroxy-4'-fluoroaurone.

* * * * *